(12) United States Patent
McGorry et al.

(10) Patent No.: US 6,651,352 B2
(45) Date of Patent: Nov. 25, 2003

(54) WRIST MOTION MEASUREMENT DEVICE

(75) Inventors: Raymond W. McGorry, Charlton, MA (US); Chien-Chi Chang, Franklin, MA (US); Patrick G. Dempsey, Franklin, MA (US)

(73) Assignee: Liberty Mutual, Hopkinton, MA (US)

( * ) Notice: Subject to any disclaimer, the term of this patent is extended or adjusted under 35 U.S.C. 154(b) by 0 days.

(21) Appl. No.: 10/038,303

(22) Filed: Jan. 4, 2002

(65) Prior Publication Data

US 2003/0126755 A1 Jul. 10, 2003

(51) Int. Cl.[7] .................................................. A61B 5/11
(52) U.S. Cl. ............................. 33/512; 33/534; 482/44; 600/595; 600/587
(58) Field of Search .................... 33/512, 511, 515, 33/534, DIG. 13; 482/8, 9, 44, 45, 47; 600/595, 587

(56) References Cited

U.S. PATENT DOCUMENTS

| | | | | |
|---|---|---|---|---|
| 4,236,528 A | * | 12/1980 | Stanec et al. | 600/554 |
| 4,747,410 A | * | 5/1988 | Cohen | 36/140 |
| 5,012,819 A | | 5/1991 | Marras et al. | |
| 5,316,017 A | * | 5/1994 | Edwards et al. | 600/595 |
| 5,471,996 A | * | 12/1995 | Boatright et al. | 600/595 |
| 5,715,834 A | * | 2/1998 | Bergamasco et al. | 600/595 |
| 5,876,363 A | * | 3/1999 | Marx | 602/21 |
| 5,980,472 A | * | 11/1999 | Seyl | 600/587 |
| 6,110,130 A | * | 8/2000 | Kramer | 600/595 |
| 6,325,768 B1 | * | 12/2001 | Williams et al. | 600/595 |
| 6,334,852 B1 | * | 1/2002 | Seyl | 600/587 |

OTHER PUBLICATIONS

Exos, Inc., Dynamic Wrist Unit (DWU™) Specifications, 1993.
Exos, Inc., Ergo Quantifier ™, 1993.
Exos, Inc., GripMaster (GM), 1994.
Neelam, Sridhar R., "Using Torque Arms to Reduce CTDs", Ergonomics in Design, Oct. 1994, pp. 25–28.
Greenleaf Medical Systems, Greenleaf Wrist System™: Advanced Sensor Technology Measuring Dynamic ROM, 1995.
Motionwatch ™, Wristcorder™, 1997, 1998.
Immersion Corporation, Cyber Glove®, 2002.
Penny & Giles Inc., Goniometers and Torsiometers, MICE (Movement. Incentive. Co–ordination. Exercise).

* cited by examiner

Primary Examiner—Christopher W. Fulton
Assistant Examiner—Amy R. Cohen
(74) Attorney, Agent, or Firm—Wolf, Greenfield & Sacks, P.C.

(57) ABSTRACT

A device and a method for measuring wrist motion is provided. The device allows for direct determination of wrist position in the radial/ulnar and flexion/extension planes, without needing calibration or determination of the center of rotation of the wrist. The goniometer forearm component is adapted to be releasably affixed to a forearm of a user. A hand component is also provided adapted to be releasably affixed to a hand of the user. The displacement measuring devices include cables adapted to be connected to the hand component. The displacement measuring devices are configured to ultimately measure angular displacement of the hand component relative to the forearm component.

55 Claims, 10 Drawing Sheets

WRIST MOTION MEASUREMENT DEVICE

FIELD OF THE INVENTION

This application relates to motion measurement devices. More particularly, this application relates to an apparatus for measuring displacement of the wrist, capable of measuring displacement in both the radial/ulnar and flexion/extension planes.

BACKGROUND OF THE INVENTION

It often is desirable to measure displacement of body parts when in motion. Such measurement may be useful in diagnosing injuries, such as loss of motion, and in studying repetitive motions to determine if such motions cause injury or strain. Knowing the position and displacement of body parts is important to biomechanical analysis. In clinical settings, motion measurement devices may provide information about motion pattern or range of motion. This knowledge may be used to determine the status of the is function of a body part and to guide treatment plans. Also, in the workplace, posture and repetitiveness of tasks may be measured. Some primary factors assessed in the workplace may include posture, force and temporal characteristics. Temporal characteristics may include the number and duration of rests and frequency of the motion. This knowledge may assist in assessing and redesigning tasks that may pose risk of injury.

Various systems have been developed for quantification of position and displacement of body parts, including active and passive cinematographic systems and electromagnetic field based systems. These systems are accurate. They tend, however, to be costly, require technical training to use, have certain technical limitations, and are generally not portable. Additionally, portable devices, such as wrist goniometer systems, require calibration for each user. For example, typically joint angular displacement at several points throughout a range are sampled, then linear regression or other techniques are used to estimate the relationship between position and transducer output. A wrist goniometer has been disclosed having two potentiometers with spring loaded cables. Individual calibration, however, is required through sampling multiple points in a range and using linear regression or similar techniques to estimate the relationship between position and transducer output.

U.S. Pat. No. 5,012,819 discloses an apparatus for monitoring the motion of components of a spine. The apparatus is mounted on the back of a patient, and includes an exoskeleton of elements which resemble the spinous process and transverse process of the spine. The elements include a central bore for receiving a cable, and three separate openings, each for receiving a wire therethrough. The cable is attached to a potentiometer which measures the twisting motion of the spine. Each of the three wires is attached to a separate potentiometer to measure flexing in the sagittal, transverse and lateral planes. The signals from the potentiometers are processed to provide a measurement of the angular position, angular velocity and angular acceleration of the spine as a function of time, for each of the three planes.

SUMMARY OF THE INVENTION

A wrist goniometer is provided that allows direct determination of wrist angular displacement in the radial/ulnar and flexion/extension planes without the necessity of extensive calibration or precise alignment relative to bone landmarks of the hand, wrist and forearm.

According to one embodiment, a goniometer is disclosed having a forearm component having at least three displacement measuring devices, and adapted to be releasably attached to a forearm of a user. A hand component is adapted to be releasably affixed to a hand of a user, and cables extending from the displacement measuring devices are adapted to be releasably connected to the hand component. The displacement measuring devices are configured to measure angular displacement of the hand component relative to the forearm component.

In one embodiment, the displacement measuring devices are configured to measure the angular displacement of the hand component relative to the forearm component on both a radial/ulnar plane and a flexion/extension plane. The cables may be under constant tension when the goniometer is in use. When the goniometer is in use on a hand and forearm of a user and viewed from above at least two cables may be substantially parallel to each other. When the goniometer is in use and on a hand and forearm of a user and viewed the side of the hand at least two cables may be substantially parallel to each other. When the goniometer is in use on a hand and forearm and viewed from the side the cables may be substantially parallel to a volar aspect of the hand and the forearm of the user when the hand and forearm are in a natural flexion position. At least first and second cables extending from the forearm component may be located at substantially the same height from a base of the forearm component. A third cable extending from a third displacement measuring device may be located at a height between the base of the forearm component and the first and second cables.

In one embodiment, at least one displacement measuring device is a potentiometer comprising a reel and a cable extending from the reel. At least the first and second cables extending from the first and second potentiometers may be located at substantially the same height from a base of the forearm component. A third cable extending from the third potentiometer may be located at a height between the base of the forearm component and the first and second cables.

In one embodiment, the hand component is a unitary piece. The cables may be releasably attached to the hand component allowing for unrestrained rotation. The hand component may include at least two pylons extending from the hand component for locating free ends of the cables. Swivel joints may releasably connect each cable adjacent a top of a pylon. A swivel joint may releasably connect a third cable to a base of a pylon. The hand component may further include a cross-member for locating the pylons on the hand component. The hand component may further include a bar for removably locating the cross-member. The bar may further include slots provided along its length, and the cross-member may include channels such that the cross-member slidably engages the bar. The cross member may be adjustably secured to the bar with at least one screw.

In one embodiment, the hand component further includes a glove for removably attaching the hand component to a hand of a user. The glove may be a palmless glove. The glove may be a fingerless glove. The hand component may further include a bar secured to the glove. The bar may be secured to the glove such that the bar is adapted for location adjacent a volar surface of a third metacarpal of a hand of a user when the glove is place on the hand of the user.

In another embodiment, the forearm component further includes a housing for mounting the displacement measuring devices. A cuff may be provided adjacent the housing and adapted for removable securement to a forearm of a user. The cuff may include at least one hinge adapted for adjustment to the forearm. The cuff may be adapted to adjust to a cross-sectional area enclosed by the cuff. The cuff may be lined with orthotic foam. The foam may be sculpted such that the foam is adapted to fit a radial and ulna of the forearm. The cuff may have a strap adapted to releasably secure the cuff to the forearm. The strap may be removably secured to the cuff with at least hook-and-loop fastener. The cuff may be a band. The band may be elasticized. The band may be a loop. The band may be formed into a loop using hook-and-loop fastener.

According to another embodiment, a goniometer is disclosed having a forearm component having at least three potentiometers adapted to be releasably affixed to a forearm of a user. A hand component is adapted to be releasably affixed on a back of a to hand of a user, and the potentiometers are adapted to be connected to the hand component. The potentiometers are configured to measure angular displacement of the hand component relative to the forearm component without calibration.

According to another embodiment, a method of determining wrist position in both flexion/extension and radial/ulnar deviation planes of movement is disclosed. The method includes the steps of providing a forearm component for locating three displacement measuring devices above a forearm of a user, providing a hand component on the back of a hand of the user, and connecting a cable from each displacement measuring device to the hand component. The displacement measuring devices are configured to measure angular displacement of the hand component relative to the forearm component in both the radial/ulnar and flexion/extension planes.

In one embodiment the method includes connecting the cables to the hand component such that they are under constant tension. The step of connecting may include locating at least a first and second cable at substantially the same height from a base of the forearm component. The step of connecting may include locating a third cable at a height between the base of the forearm component and the first and second cables. The displacement measuring device may be a potentiometer including a reel and a cable extending from the reel. The step of connecting may include connecting the first and second cables from the first and second potentiometers to the hand component such that the cables are located at substantially the same height from a base of the forearm component and are substantially parallel to each other. The step of connecting may include extending a third cable from the third potentiometer to locate the cable at a height between the base of the forearm component and the first and second cables such that the third cable is substantially parallel to at least one of the first and second cables.

In one embodiment, the step of providing a hand component includes providing at least two pylons for connecting ends of the cables to the hand component. The step of connecting may include connecting the cables to the pylons with swivel joints. The step of connecting may include attaching the cables to the pylons to allow for unrestrained rotation. The step of connecting may include providing a cross-member for locating the pylons on the hand component. The step of connecting may include removably locating the cross-member on a bar of the hand component. The step of connecting may include removably securing the cross-member to the bar with screws.

In one embodiment, the step of providing the hand component includes attaching the hand component onto a glove for removably locating the hand component on the back of a hand of the user. The step of providing the hand component may include locating the hand component such that it is adjacent the volar surface of the third medicarpal on a hand of a user. The step of providing the forearm component may include mounting the displacement measuring devices on a housing of the forearm component. The step of providing the forearm component may include securing the forearm component to a forearm of a user by a cuff. The step of providing the forearm component may include adjusting cross-sectional area enclosed by the cuff. The step of providing the forearm component may include releasably securing the cuff to a forearm of a user with a strap. The step of providing the forearm component may include releasably securing the cuff to a forearm of a user with hook-and-loop fastener.

BRIEF DESCRIPTION OF THE DRAWINGS

Other features and advantages of the invention will become apparent from the following detailed description taken in conjunction with the accompanying drawings, in which.

DETAILED DESCRIPTION

Figure 10:
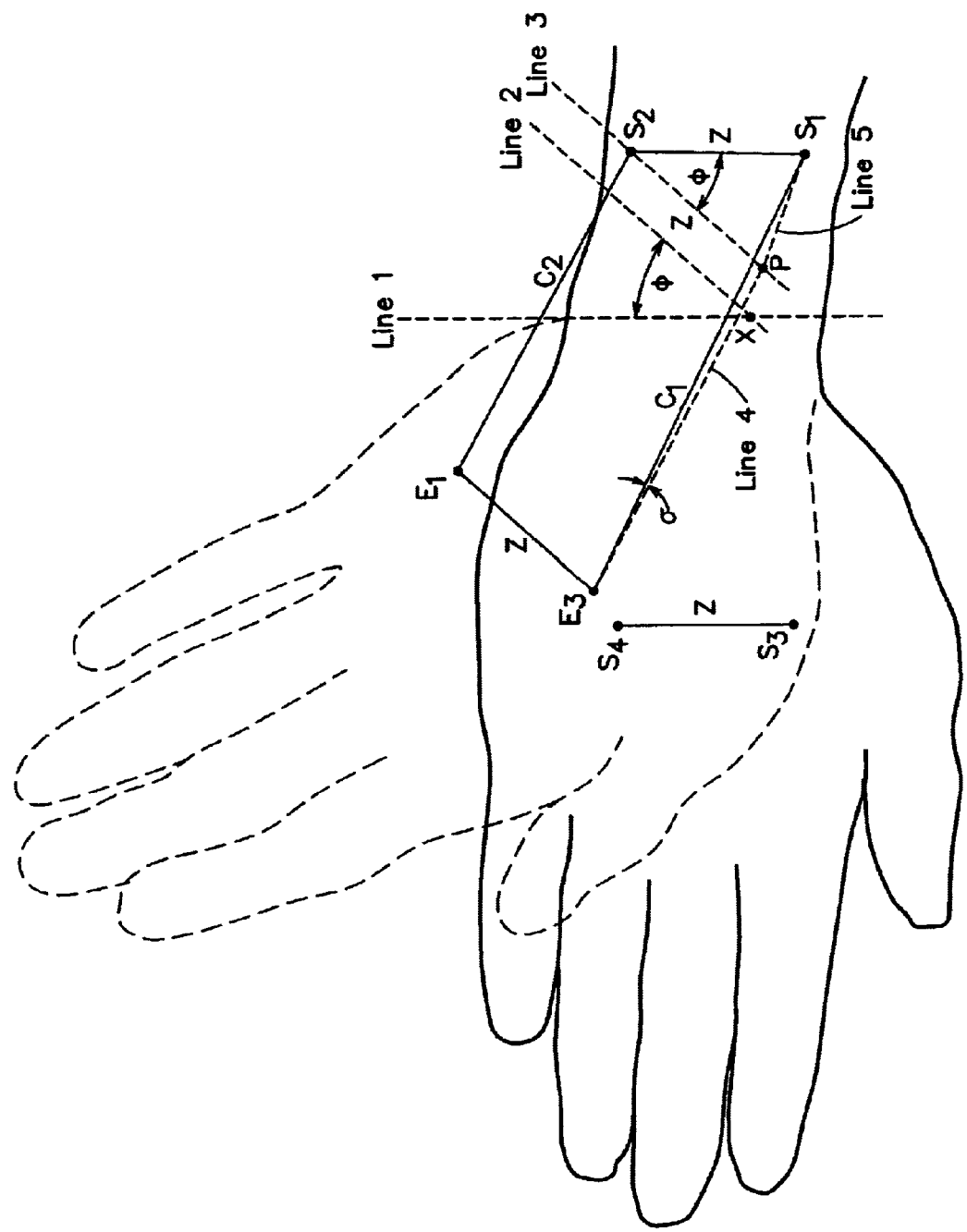
FIG. 10 is a plan view of the right hand displaying the geometry according to an embodiment of the invention.
Figure 11:
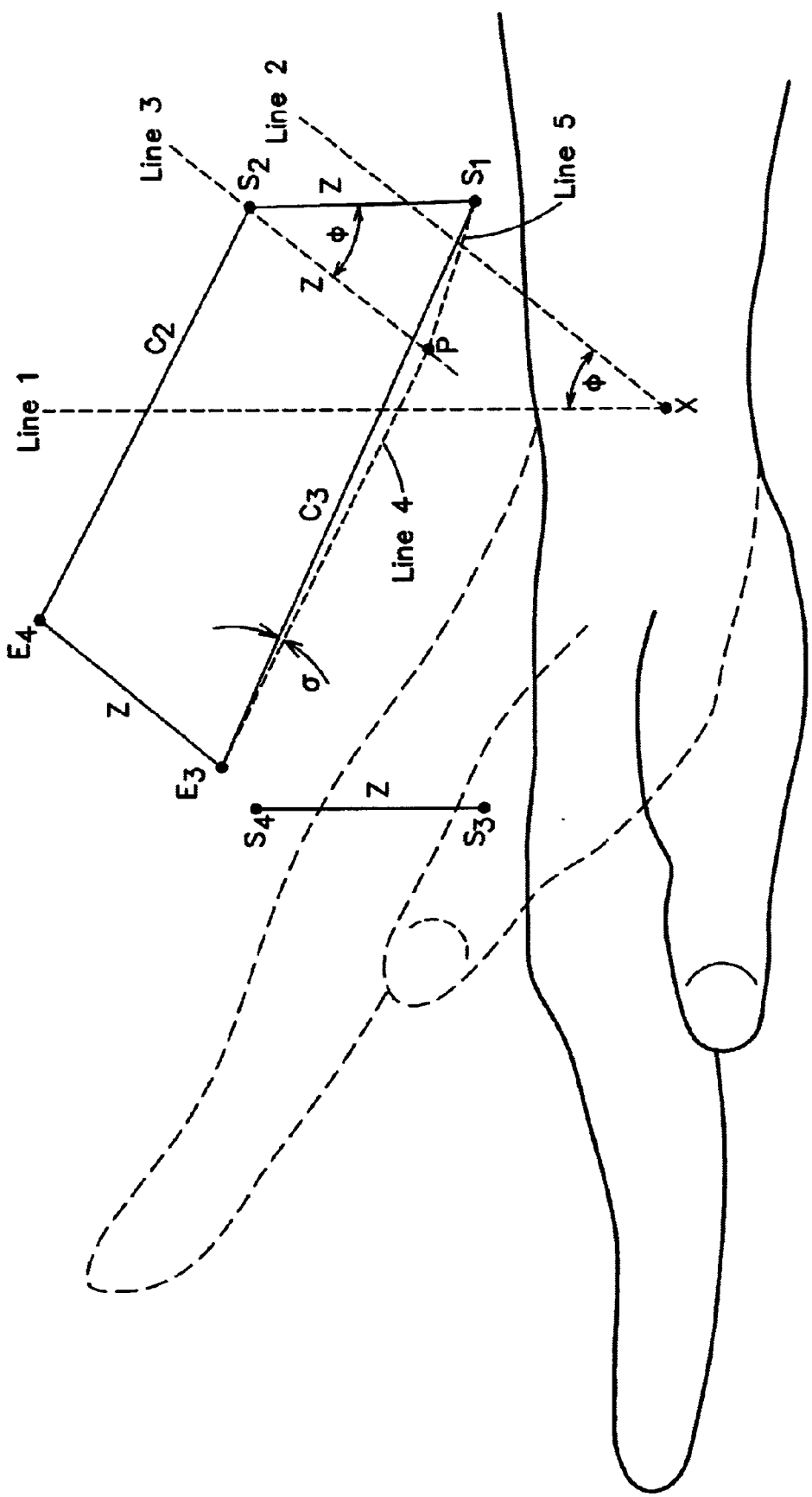
FIG. 11 is a plan view of the medial side of the right hand displaying the geometry according to an embodiment of the invention.

The invention discloses a goniometer usable to determine wrist position in two orthogonal planes, such as both in a radial/ulnar (hereinafter R/U) plane of movement and in a flexion/extension (hereinafter F/E) plane of movement. The R/U plane of movement is shown in FIG. 10, and is movement within the XY or horizontal plane such as occurs when the hand is moved side-to-side. The F/E plane of movement is shown in FIG. 11, and is movement within the YZ or vertical plane such as occurs when the hand is moved up and down. Wrist angular displacement is tracked based on the differences in length between two parallel sides of a quadrilateral, and these are used to calculate the angle of one adjacent side to the other. A goniometer is disclosed that provides for direct determination of angular displacement on two orthogonal planes, such as the R/U and F/E planes, preferably without the need for calibrating the device and/or without precise alignment relative to bone landmarks of a hand. In one embodiment, a goniometer is provided having a hand component and a forearm component. The forearm component includes three displacement measuring devices with cables removably secured to the hand component.

Figure 1:
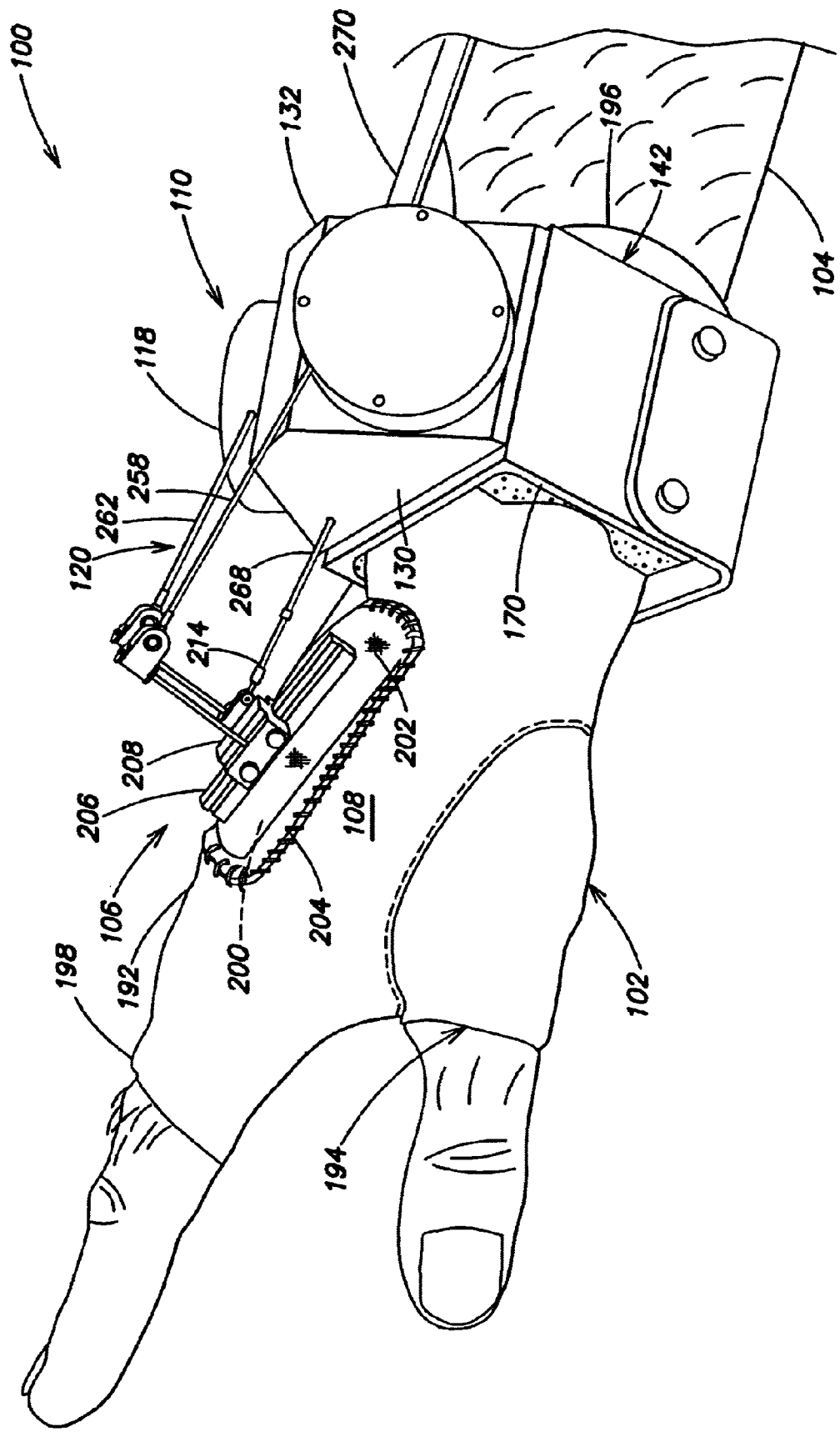
FIG. 1 is a perspective view of a goniometer according to an embodiment of the invention.
Figure 2:
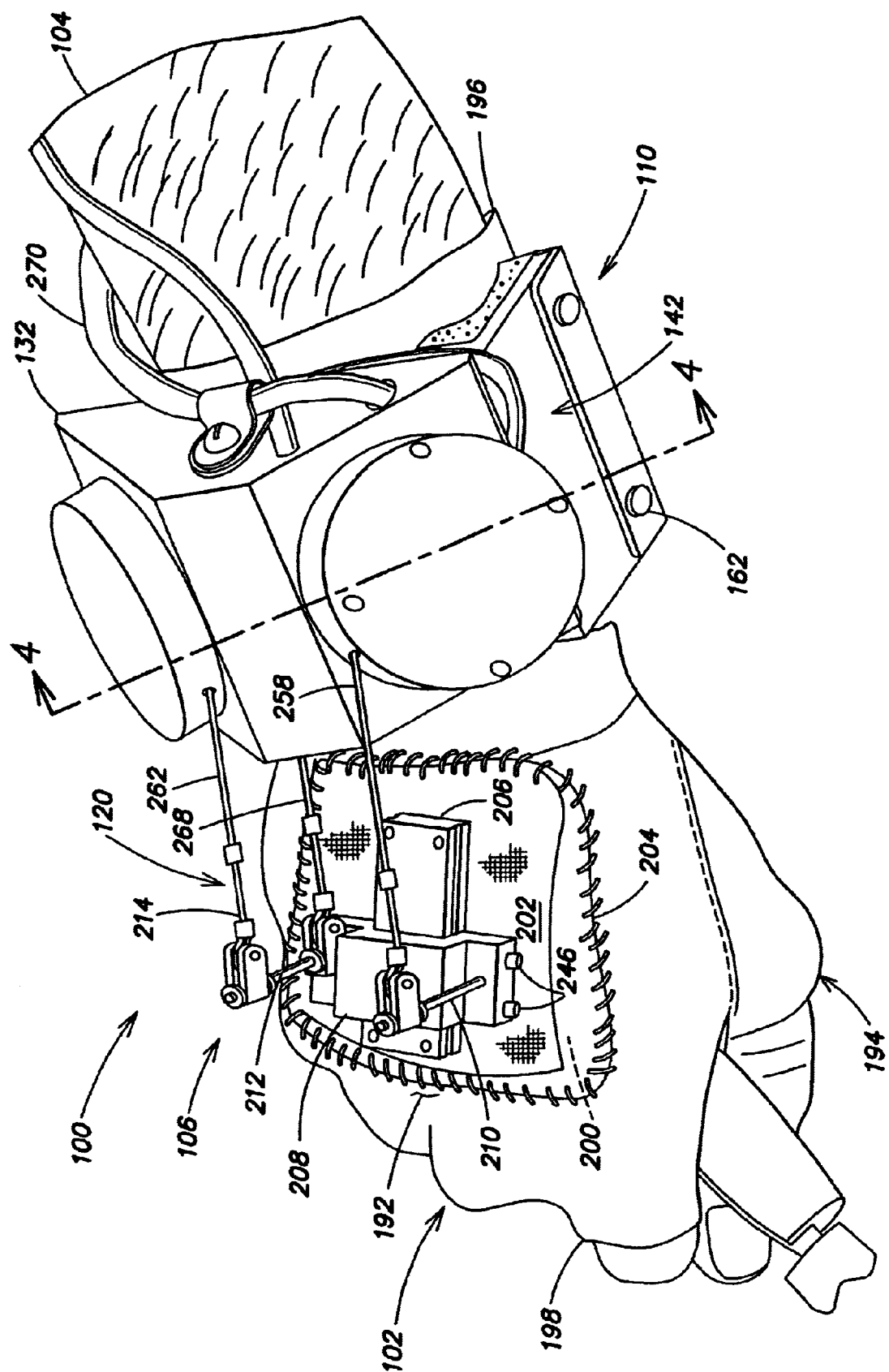
FIG. 2 is a perspective view of the goniometer of FIG. 1.
Figure 3:
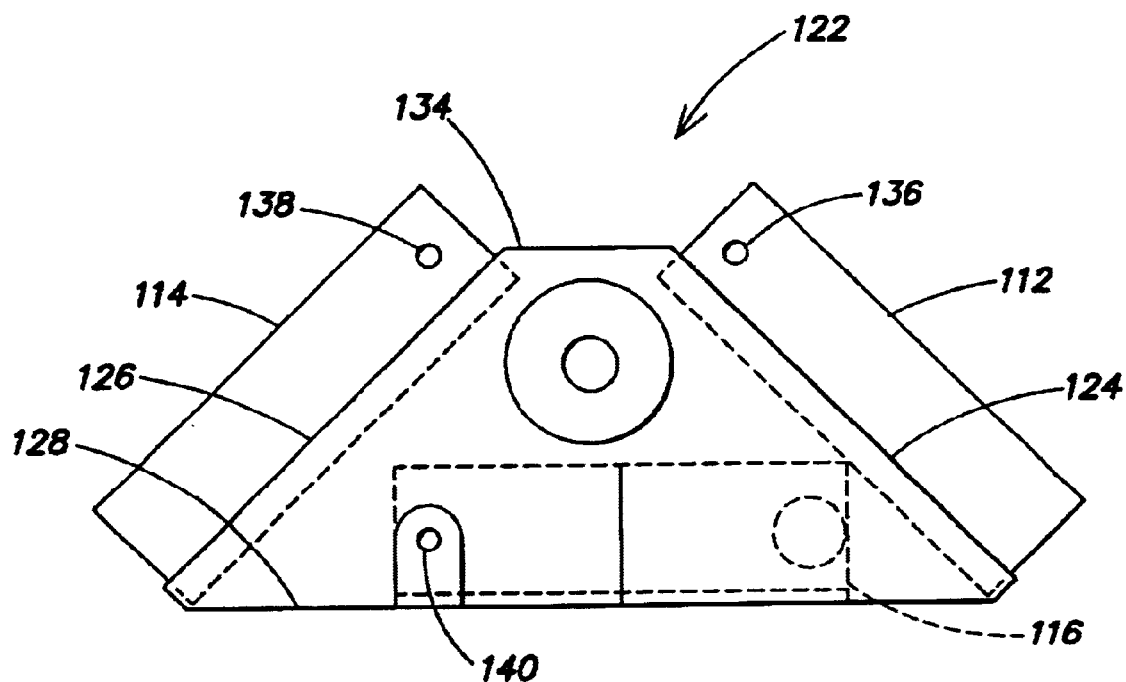
FIG. 3 is a front view of the mounting block and displacement measuring devices of FIG. 1.

Referring to FIGS. 1 and 2, a goniometer 100 according to the invention is shown on a hand 102 and a forearm 104 of a user. A hand component 106 is removably secured to a back 108 of the hand 102 and a forearm component 110 is removably secured to the forearm 104. The forearm component 110 includes three displacement measuring devices 112, 114 and 116 (FIG. 3). Although any displacement measuring device may be used, preferably the displacement measuring devices 112, 114 and 116 are spring loaded cable displacement position potentiometers, such as Model 174 manufactured by Space Age Controls, Inc. of Palmdale, Calif. The displacement measuring devices 112, 114 and 116 are used to track position of the hand 102 relative to the forearm 104. Typically, the displacement measuring devices 112, 114 and 116 feature reels 118 and cables 120.

Figure 4:
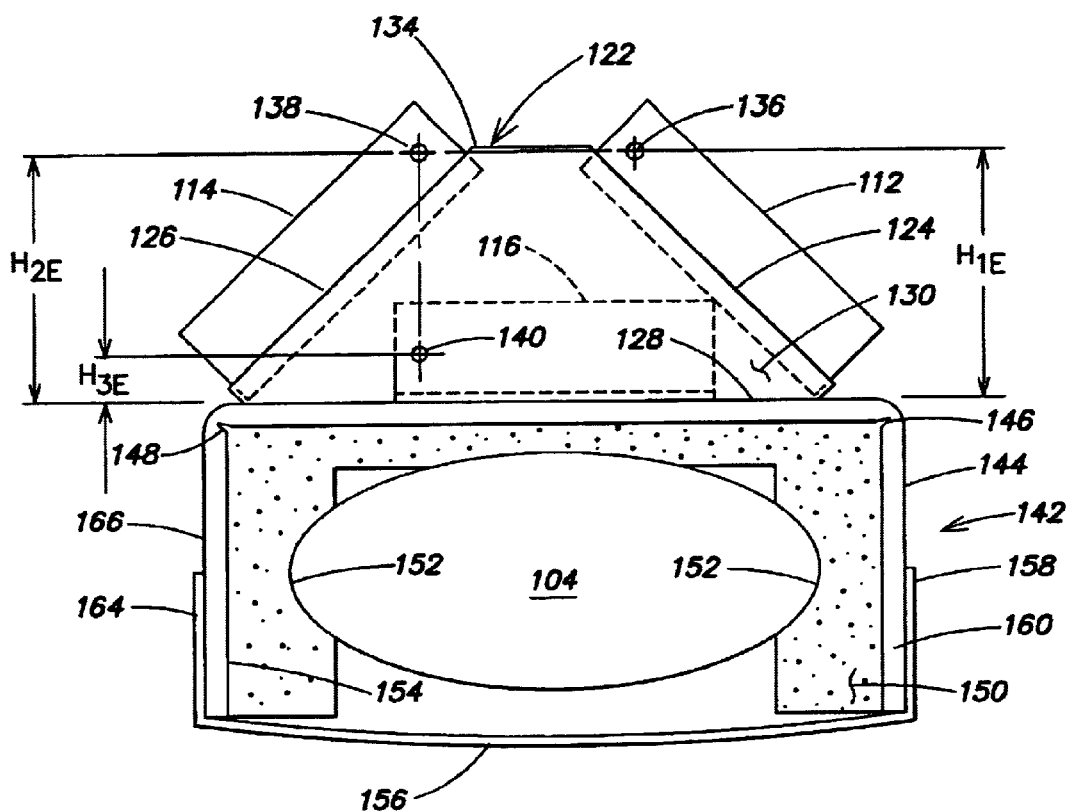
FIG. 4 is a cross-sectional view of the wrist mount with the mounting block and displacement measuring devices taken along line 4—4 of FIG. 2.
Figures 7A, 7B:
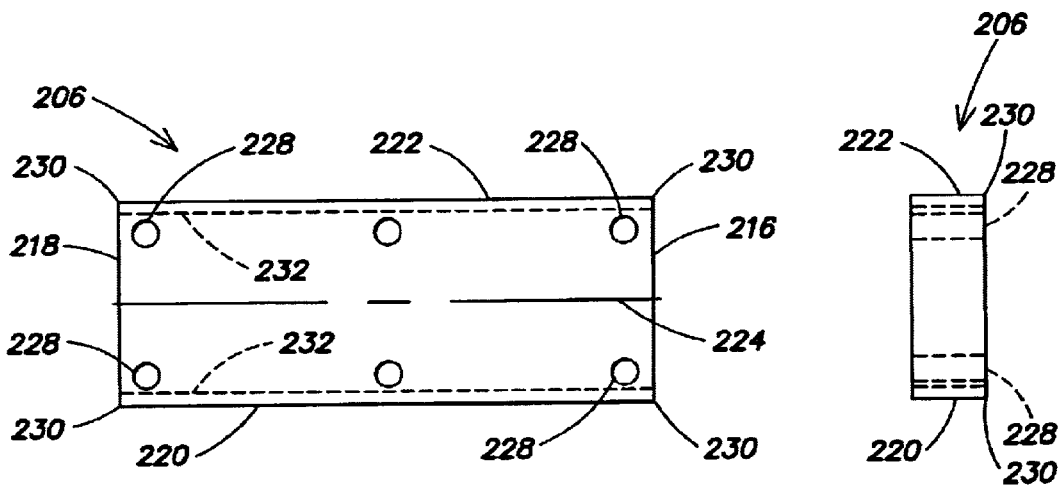
FIG. 7A is a top view of a guide block according to an embodiment of the invention.
FIG. 7B is a front view of the guide block of FIG. 7A.

As shown in FIGS. 3–4, the displacement measuring devices 112, 114 and 116 are provided on a housing 122. The housing 122 is made of plastic, although it could be made of any suitable material. As shown, the housing 122 has a triangular shape having first, second and third sides 124, 126 and 128 between two housing ends 130 and 132 (FIG. 1) with an apex 134 of the triangle being flat. It will be appreciated that the housing 122 may have any suitable size and shape, not just the shape shown in the illustrated embodiments in the drawings. The smaller and lower the profile of the housing and the less it weighs, the less the forearm component will move about the forearm of the user providing more accurate and consistent measurements. The triangular shape shown locates two of the displacement measuring devices 112 and 114 on opposite first and second sides 124 and 126 of the triangular housing 122 angled toward one another, while the third displacement measuring device 116 is provided on the third side 128 of and within the triangular housing 122. The displacement measuring devices may be attached to the housing by any suitable manner, such as adhesive.

The displacement measuring devices 112, 114 and 116 are located such that cables 120 exit the devices at particular positions. As illustrated, preferably first and second exit positions 136 and 138 for the first and second displacement measuring devices 112 and 114 are aligned such that the cables will extend within the same horizontal XY plane. A third exit position 140 of the third displacement measuring device 116 is preferably aligned vertically with one of the exit positions 136 and 138 of the first or second displacement measuring device 112 and 114. As shown, the third exit position 140 is vertically aligned with the second exit position 138 such that the aligned cables will extend through the vertical YZ plane.

Referring to FIG. 4, the housing 122 is shown provided on a cuff 142 for mounting to a forearm 104 of a user. The housing 122 may be removably or permanently mounted to the cuff 142 in any suitable manner, for example with adhesive, rivets, screws, hook-and-loop fastener and/or the like. The cuff 142 may be hinged and may have an adjustable width. As shown in FIG. 4, the cuff 142 may have an outer portion 144 with two hinges 146 and 148. The hinges 146 and 148 assist in accommodating a forearm and securely mounting the cuff 142 with the forearm component 110 to a forearm 104 of a user. As shown in FIG. 4, the cuff 142 may feature orthotic foam 150 sculpted to fit around a radius and ulna of a forearm. The foam 150 may feature sculpted parts 152 to accommodate the forearm. As shown, the foam 150 is provided on an inside surface 154 of the outer portion 144 of the cuff 142. The foam 150 may be secured to the outer portion 144 of the cuff 142 using an adhesive preferably, a high strength adhesive.

The cuff 142 is secured to a forearm 104 using a strap 156. The strap 156 may be secured on a first end 158 to a first side 160 of the outer portion 144 using fastening devices 162 (FIG. 2), such as rivets, screws, nails, bolts and/or the like. A free end 164 may be removably secured to a second side 166 of the outer portion 144 of the cuff 142, by a fastening device such as a hook-and-loop fastener, snaps and/or the like. The cuff 142 is placed on the forearm and the free end 164 of the strap 156 is secured to the second side 166 of the outer portion 144 of the cuff 142. Preferably, an edge 170 (FIG. 1) of the cuff closest to the edge of the forearm near the wrist is 2 or 3 cm from the line between the styloid process and the head of the ulna.

Figure 5:
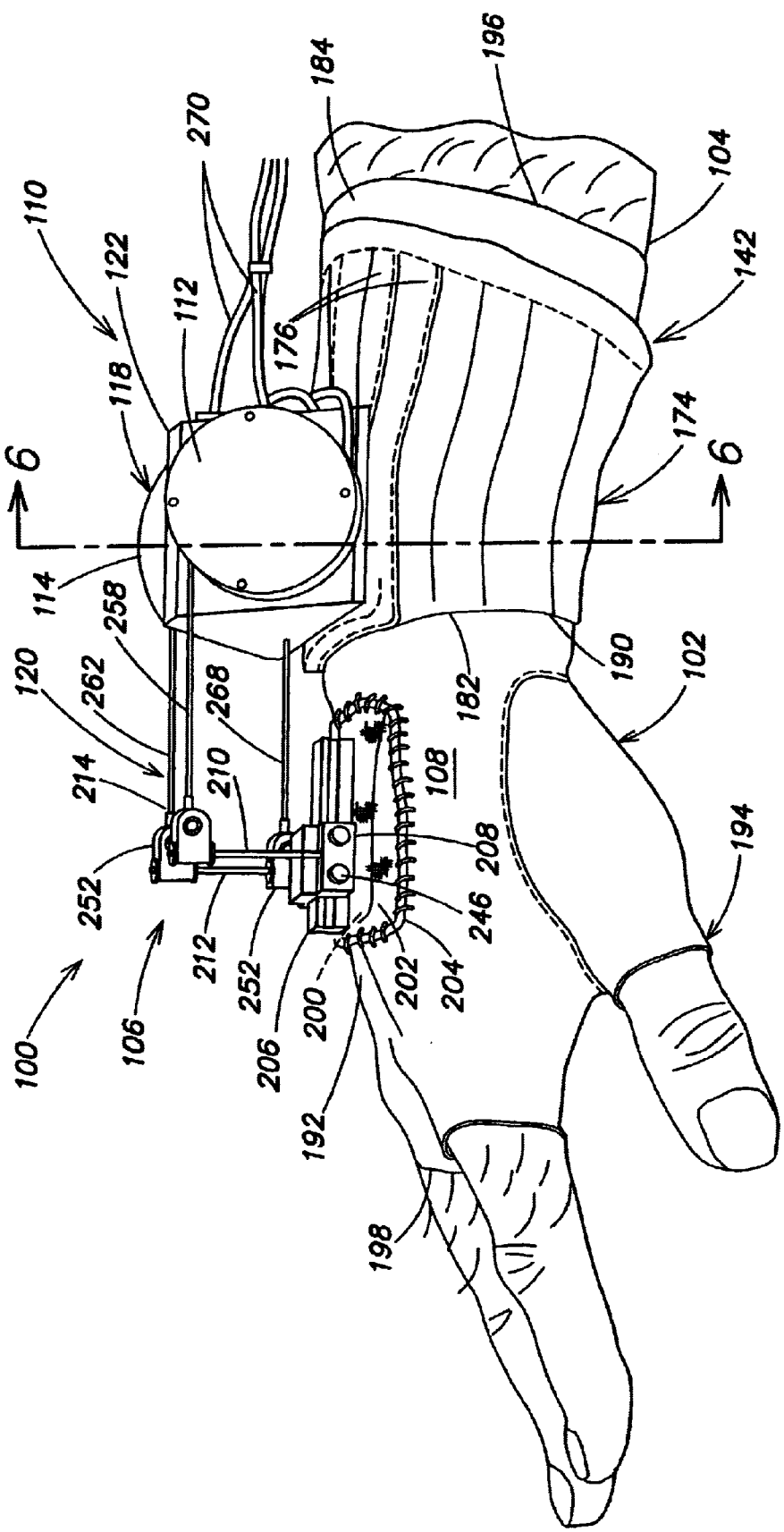
FIG. 5 is a perspective view of a goniometer according to another embodiment of the invention.
Figure 6:
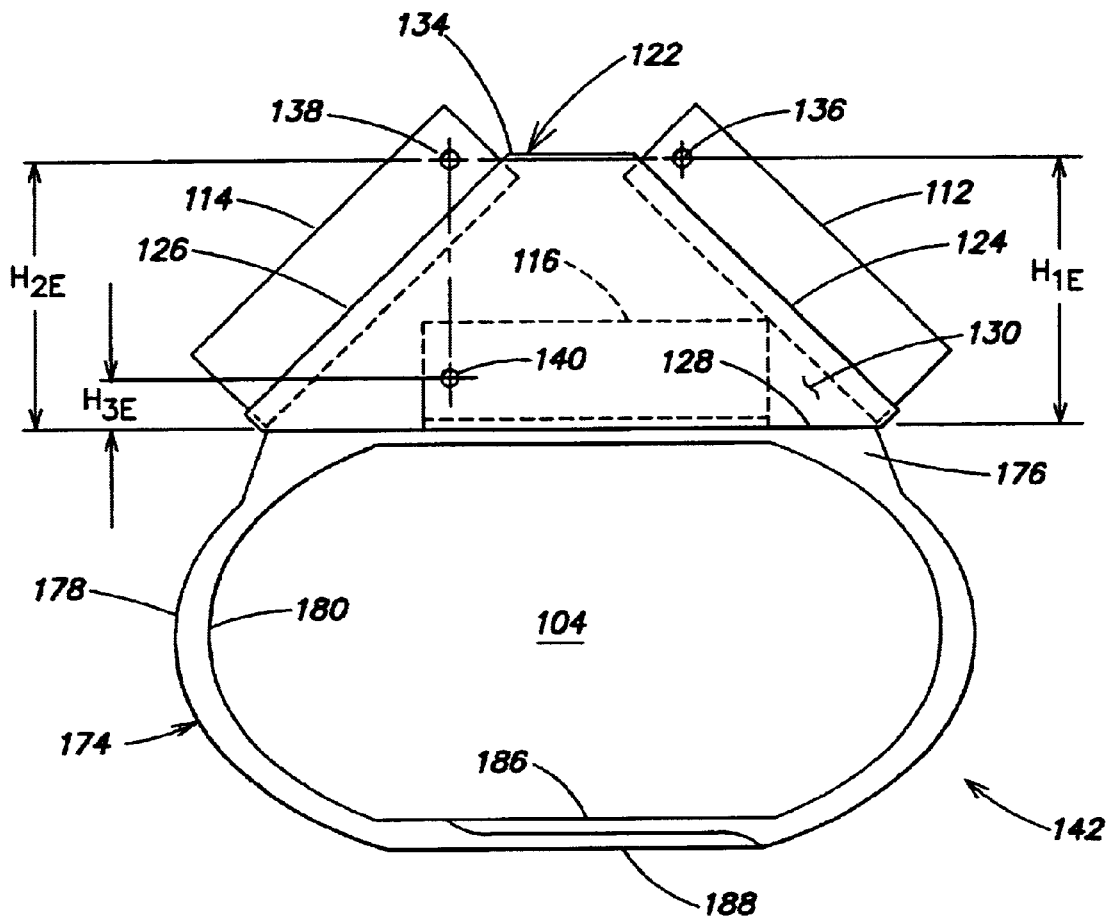
FIG. 6 is a cross-sectional view of the wrist mount with the mounting block and displacement measuring devices to taken along line 6—6 of FIG. 5.
Figure 8A:
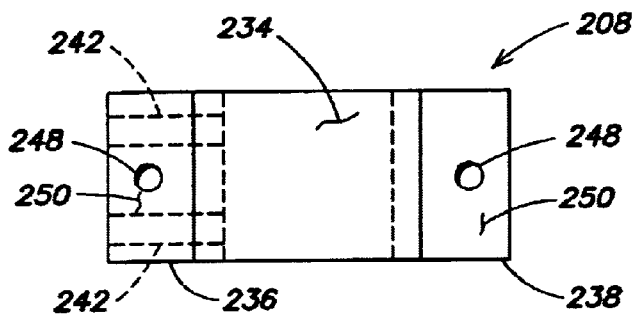
FIG. 8A is a top view of the cross member according to an embodiment of the invention.
Figure 8B:
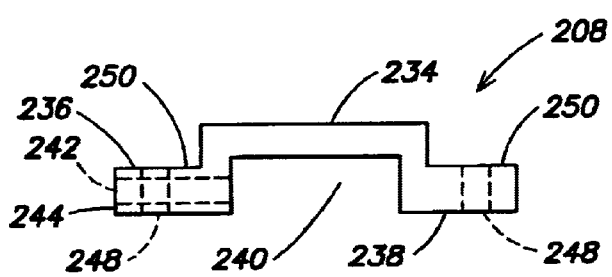
FIG. 8B is a front view of the cross member of FIG. 8A.
Figure 8C:
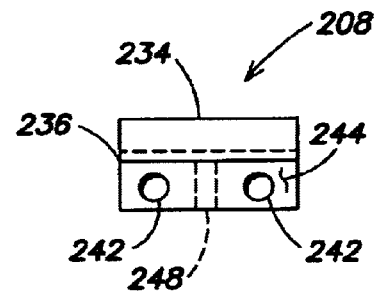
FIG. 8C is a side view of the cross member of FIG. 8A.

Referring to FIGS. 5 and 6, a preferred embodiment of the cuff 142 for use with the invention is illustrated. The housing 122 shown in FIGS. 5 and 6 is substantially the same as that of FIGS. 3 and 4. The cuff 142 features a forearm support 172, such as an elasticized forearm band 174. The forearm band 174 may be made at least partially of nylon and/or spandex. The elasticized forearm band 174 may feature stays 176 for additional support provided along the length of the forearm band 174, particularly where the forearm component 110 is mounted. The stays 176 may be made of any suitable material, such as plastic. The stays 176 may be mounted on the elasticized forearm band 174 on an outer or inner surface 178 or 180 thereof or may be incorporated within the forearm band 174. The forearm component 110 may be mounted to the forearm band 174 in any suitable manner, such as by adhesive, rivets, screws, hook-and loop fastener and/or the like. The forearm component 110 may be secured directly to the stays 176 and/or to the forearm band 174.

The forearm band 174 is a loop with first and second open ends 182 and 184. The forearm band 174 may be slipped over the user's hand and onto the forearm such that the forearm band 174 resides around the forearm. Alternatively, the forearm band 174 is not provided as a loop, but a rectangular shape with two sides 186 and 188 provided between the two ends 182 and 184. The two sides 186 and 188 (FIG. 6) may be removably mated together, for example with hook-and-loop fastener to form a loop. Thus, the forearm band 174 is removably secured to the forearm by attaching the two sides 186 and 188 of the forearm band 174. This construction allows the forearm band 174 to fit a wide range of differently sized forearms. The forearm band 174 is preferably provided such that an edge 190 of the band closest to the edge of the forearm near the wrist is approximately 2 cm from the line between the styloid process of the radius and the head of the ulna.

Referring now to FIGS. 1, 2 and 5, the hand component 106 will now be discussed. The hand component 106 is removably secured to the back 108 of the hand 102 by any suitable manner. As illustrated, the hand component 106 is secured to a back 192 of a glove 194, such that placement of the glove 194 on a hand locates the hand component 106 in the desired position on the back 108 of the hand 102. Preferably, the glove 194 is a tight fitting glove, such as an elasticized glove. The glove 194 may be made at least partially of nylon and/or spandex. The glove 194 features an open end 196 opposite a finger end 198 of the glove 194 for inserting the hand into the glove 194. As shown, the open end 196 is provided on the user's forearm such that a substantial portion of the forearm of the user is covered by the glove 194. The cuff 142 of the forearm component 110 may be placed over the glove 194 on the forearm for additional stability. It will be understood that the glove 194 may feature an open end 196 that ends adjacent the wrist of the user such that the glove 194 does not fit on a part or all of the forearm of the user. Additionally, the glove 194 may be fingerless and/or palmless to allow the user to more easily perform tasks without the glove obstructing their performance of the tasks.

As shown in FIGS. 1, 2 and 5, the hand component 106 is secured to the glove 194. The hand component 106 is mounted to a plate 200 which is secured to the glove 194. It will be understood that the plate 200 may be secured to the glove 194 in any suitable manner. The plate 200 may include a textile 202 secured to the top of the plate 200, such as by adhesive. The plate 200 and textile 202 may then be secured to the glove 194 in any suitable manner, for example by adhesive and/or sewing. Edges 204 of the textile 202 may be sewn to the glove 194. The hand component 106 may be secured directly to the plate 200 and/or to the textile 202, if present, in any suitable manner such as with adhesive, screws, rivets and/or the like.

As shown, the hand component 106 includes a slotted bar 206. In the illustrated embodiment, a cross-member 208 interfits over the slotted bar 206 and two pylons 210 and 212 rise from the slotted bar 206 which receive the free ends 214 of the cables from the displacement measuring devices 112, 114 and 116. It will be understood that the hand component may be placed in any suitable location on the a back of a hand. Moreover, it will be appreciated that the hand component 106 may be made in any suitable shape and may be a one-piece or multiple-piece unit. The smaller and lower the profile of the hand component and the less it weighs, the less the hand component will move about the hand of the user and the more accurate and consistent the measurements. The hand component 106 may be made in any suitable manner such as by molding and/or machining.

Referring to FIGS. 1, 2, 5, 7A and 7B, the slotted bar 206 is shown. The slotted bar 206 is rectangular in shape having two ends 216 and 218 connected by two sides 220 and 222. It will be appreciated that any suitable shape for the slotted bar 206 may be 523886 used. The sides 220 and 222 of the slotted bar 206 form a longitudinal axis 224 of the slotted bar 206 which is preferably placed along the volar surface of the third metacarpal of the hand of the user. The slotted bar 206 is secured to the plate 200 by any suitable manner. As shown, the slotted bar 206 is secured to the plate by a screw through a hole 228 provided in each corner 230 of the slotted bar 206. The sides 220 and 222 of the slotted bar 206 each feature a slot 232 running along the length of the sides 220 and 222. The slotted bar 206 is made of plastic, although any suitable material may be used.

Referring to FIGS. 1, 2, 5 and 8A–C, the cross-member 208 is shown. The cross-member 208 is removably secured to the slotted bar 206. The cross-member 208 fits slidingly onto the slotted bar 206 by engaging the slots 232 of the slotted bar 206, for example with channels. The cross-member 208 may be located anywhere along the length of the slotted bar 206. As shown, the cross-member 208 has a shape with a raised middle section 234 between two end sections 236 and 238. An open area 240 is formed underneath the middle section 234 between the end sections 236 and 238 to accommodate the slotted bar 206. It will be appreciated, however, that any suitable shape for the cross-member may be used. One side section 236 of the cross-member 208 features at least one cross-hole 242 extending from an end 244 through the end section 236 to the open area 240 of the cross-member 208 for receiving a screw 246 (FIG. 2) to secure the cross-member 208 to the slotted bar 206 at a desired location along the length of the slotted bar 206. As shown, two cross-holes 242 are provided through the end section 236. The cross-member 208 may be made of any suitable material, such as plastic.

Additionally, a pylon receiving hole 248 is provided on a top surface 250, of each end section 236 and 238 of the cross-member 208 for receiving a pylon 210 and 212. As shown the cross-member 208 and pylons 210 and 212, are made as separate pieces. It will be understood that they could be formed as one piece, for example by machining or molding. Moreover, the pylons 210 and 212 could take on numerous different shapes. For example, instead of two pylons a single block could extend from the cross-member 208.

Figure 9:
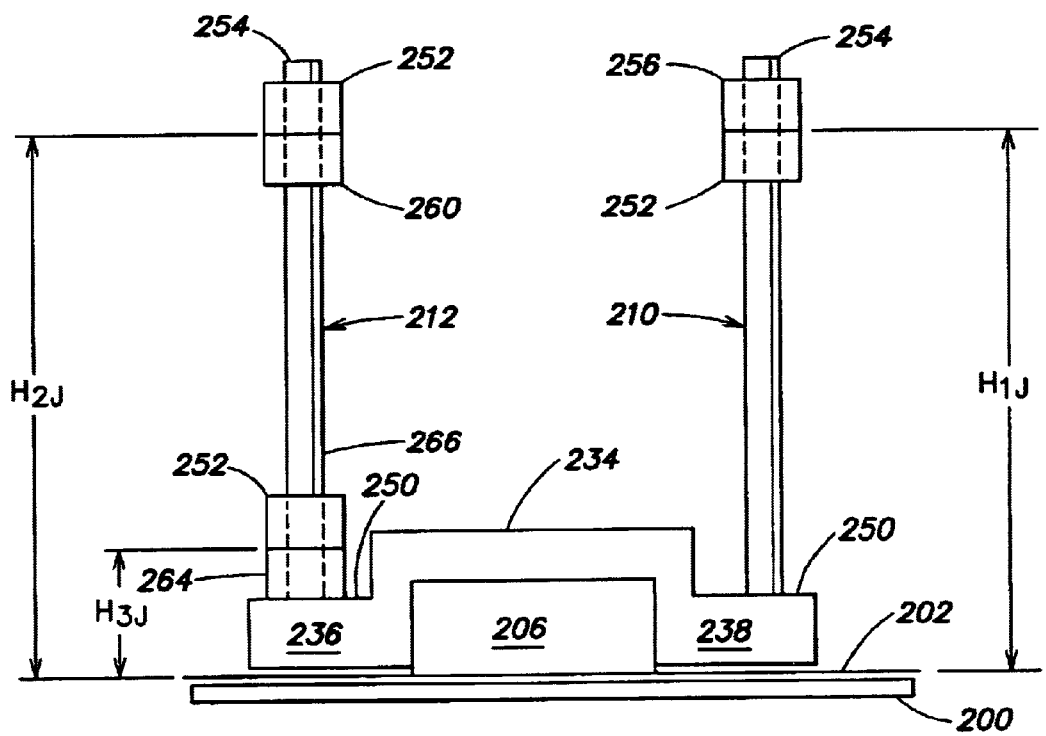
FIG. 9 is a front view of an assembled hand component according to an embodiment of the invention.

Referring to FIG. 9, the assembled hand component 206 is shown. The pylons 210 and 212 extend substantially perpendicular to the top surfaces 250 of the end sections 236 and 238 of the cross-member 208. The pylons 210 and 212 are made of steel, although any suitable material may be used. The pylons 210 and 212 feature receiving devices 252 for removably connecting with the free ends 214 of the cables 120. As shown, each pylon 210 and 212 features a receiving device 252 adjacent a top 254 of the pylon 210 and 212 and one of the pylons 212 includes a third receiving device 252 for the third cable 120 adjacent a base 266 of the pylon 212. Preferably, the receiving devices 252 are swivel joints and/or allow unrestricted rotation of the cable free ends 214 about the pylons 210 and 212 in both the R/U and F/E planes. The cables 120 are made of steel, although any suitable material may be used. It is preferable the material used have a minimum increase in length over time due to stretching. A light, constant tension may be maintained in the cables 120 by springs intrinsic to the cables of the displacement measuring devices 112, 114 and 116.

As shown, the first pylon 210 features a first swivel joint 256 adjacent the top 254 of the first pylon 210 for receiving a first cable 258 (FIGS. 1, 2 and 5). When in use, the height $H_{1E}$ (FIGS. 4 and 6) of the first exit position 136 of the first cable 258 (FIGS. 1, 2 and 5) from the first displacement measuring device 112 is substantially the same as the height $H_{1J}$ (FIG. 9) of the first swivel joint 256 on the first pylon 210. The second pylon 212 features a second swivel joint 260 adjacent the top 254 of the second pylon 212 for receiving a second cable 262 (FIGS. 1, 2 and 5). When in use, the height $H_{2E}$ (FIGS. 4 and 6) of the second exit position 138 of the second cable 262 (FIGS. 1, 2 and 5) from the second displacement measuring device 114 is substantially the same as the height $H_{2J}$ (FIG. 9) of the second swivel joint 260 on the second pylon 212. The second pylon 212 also features a third swivel joint 264 adjacent the base 266 of the second pylon 212 for receiving a third cable 268 (FIGS. 1, 2 and 5). When in use, the height H3E (FIGS. 4 and 6) of the third exit position 140 of the third cable 268 (FIGS. 1, 2 and 5) from the third displacement measuring device 116 is substantially the same as the height $H_{3J}$ (FIGS. 9) of the third swivel joint 264 on the second pylon 212. Thus, the first, second and third cables 258, 262 and 268 are substantially parallel to each other when viewed from the side of the goniometer 100 and the second and third cables reside substantially in the same YZ or F/E plane. The first, second and third cables 258, 262 and 268 are substantially parallel to each other when viewed from above the top of the goniometer 100 and the first and second cables reside substantially in the same XY or R/U plane.

When placing the goniometer 100 on a user's hand 102 and forearm 104, typically the user's hand 102 is first placed in the glove 194 having the hand component 106, such that the longitudinal axis 224 of the slotted bar 206 of the hand component 106 is placed along the volar surface of the third metacarpal. The cuff 142 having the forearm component 110 is then provided on the user's forearm 104 over the glove 194. For convenience, the cables 258, 262 and 268 may be kept secured to the swivel joints 256, 260 and 264 on the pylons 210 and 212 and thereby to the cross-member 208. After the glove 194 and cuff 142 have been respectively secured to the user's hand 102 and forearm 104, the cross-member 208 may be engaged with the slots 232 in the slotted bar 206, placed at the desired location along the length of the slotted bar 206, and screws 246 may be inserted into the cross-holes 242 to secure the cross-member 208 into position on the slotted bar 206. Thus, the goniometer 100 is ready for use. It will be appreciated that the cross-member may be secured to the slotted bar at anytime and the cables may be secured to the swivel joints of the cross-member any time before or after securement of the cross-member to the slotted bar.

Wires 270 to the displacement measuring devices 112, 114 and 116 extend from the displacement measuring devices 112, 114 and 116 out the second end 132 of the housing 122 and may be connected to an A/D converter, sampled at 100 Hz, and the output data may be stored in a computer file to be analyzed later. The output data of the displacement measuring devices 112, 114 and 116 may be used to determine the angular displacements in the R/U and F/E planes. Output data from the displacement measuring devices 112, 114 and 116 may also be collected in a computerized spreadsheet program. An IBM PC compatible computer may be used to acquire data, but the analog output from the displacement measuring devices could be passed to any suitable microprocessor based device with processing analog to digital conversion capability. A palm sized computer may also be used and may be capable of displaying real-time angular displacement data, providing a very compact system important in some field applications. The method described below may be used to determine the angular displacement in the R/U and F/E planes based on the output data from the displacement measuring devices 112, 114 and 116.

Referring to FIGS. 10 and 11, a discussion of a method of determining the angular displacement of the hand component 106 relative to the forearm component 110 in both R/U and F/E planes will be discussed. The difference in cable length of co-planar displacement measuring devices 112, 114 and 116 can be used to directly calculate a trigonometric solution of the angular displacement of the hand component 106 relative to the forearm component 110 in both the R/U and F/E planes. It will be appreciated that although a preferred method is described below, any suitable manner for calculating the angular displacement of the hand component relative to the forearm component may be used.

FIG. 10 presents a view of the volar aspect of a right hand deviating radially by $\phi$ degrees about the joint center X from a starting position to an end position in the R/U plane. The relative differences in length of the first cable 258 and the second cable 262 are used to calculate the trigonometric solution for angular displacement in the R/U plane. The points $S_1$ and $S_2$ represent the cable origins at the first and second exit positions 136 and 138 from the forearm component 110 at the starting position. The points $S_3$ and $S_4$ represent the starting position of the cable free ends 214 at the pylons 210 and 212 located on the hand component 106. Points $E_3$ and $E_4$ represent the end position of the cable free ends 214 at the pylons 210 and 212 located on the hand component 106 after movement of the hand. The lengths of the line segments $\overline{S_1S_2}$, $\overline{S_3S_4}$, and $\overline{E_3E_4}$ are of fixed and preferably substantially equal length z. The center of rotation of the wrist X is assumed to be located between line segment $\overline{S_1S_2}$ on the forearm component 110, and line segment $\overline{S_3S_4}$ on the hand component 106. As shown, the location of the center of the rotation of the wrist X is not constrained to below line segment $\overline{S_2S_4}$ or above line segment $\overline{S_1S_3}$.

Line 1 is constructed substantially parallel to line segments $\overline{S_1S_2}$ and $\overline{S_3S_4}$, and passes through the center of rotation X. Lines 2 and 3, are constructed substantially parallel to line segment $\overline{E_3E_4}$ and pass through the center of the rotation of the wrist X and the point $S_2$, respectively. The angle $\phi$ is provided between Line 1 and Line 2, and between Line 3 and line segment $\overline{S_1S_2}$. Line segments $\overline{E_3S_1}$ and $\overline{E_4S_2}$ represent the first and second cables 258 and 262 of the first and second displacement measuring devices 112 and 114 having lengths $C_1$ and $C_2$, respectively. Line 4 is constructed substantially parallel to line segment $\overline{E_4S_2}$ and passes through point $E_3$, and intersects Line 3 at point P. A parallelogram is formed by line segment $\overline{E_4S_2}$, line segment $\overline{E_3E_4}$, Line 4, and the line segment $\overline{PS_2}$, which lies along Line 3. The line segment $\overline{PS_2}$ is substantially equal to line segment $\overline{E_3E_4}$, and both have a length z. An angle $\sigma$ is provided between Line 4 and line segment $\overline{E_3S_1}$. Additionally, line segment $\overline{PS_1}$ lies along Line 5.

For triangles $\Delta P\ E_3\ S_1$, and $\Delta P\ S_2S_1$, the law of cosines ($c^2 = a^2 + b^2 - 2^{ab} \cos C$) can be applied to create the following two equations:

$$\overline{PS_1}^2 = \overline{E_3S_1}^2 + \overline{PE_3}^2 - 2 \cdot \overline{E_3S_1} \cdot \overline{PE_3} \cdot \cos \sigma \tag{1}$$

and;

$$\overline{PS_1}^2 = \overline{PS_2}^2 + \overline{S_1S_2}^2 - 2 \cdot \overline{PS_2} \cdot \overline{S_1S_2} \cdot \cos \phi \tag{2}$$

Substituting (2) in to (1);

$$\overline{E_3S_1}^2 + \overline{E_4S_2}^2 - 2 \cdot \overline{E_3S_1}^3 \cdot fheight\overline{PE_3} \cdot \cos \sigma = \overline{PS_2}^2 + \overline{S_1S_2}^2 - \overline{PS_2} \cdot S1S\ 2 \cdot \cos \phi \tag{3}$$

The following values are known:

$\overline{S_1S_2} = z$ (fixed by hardware), $\overline{PS_2} = z$ (by definition), $\overline{E_3S_1} = C_1$ (is the length of the first cable 258 of the first displacement measuring device 112), $\overline{E_4S_2} = C_2$ (is the length of the second cable 262 of the second displacement measuring device 114), $\overline{PE_3} = C_2$ (by definition), substituting the above values into (3) yields the following:

$$C_1^2 + C_2^2 - 2 \cdot C_1 \cdot C_2 \cdot \cos \sigma = z^2 + z^2 - 2 \cdot z \cdot z\ \cos \phi, \text{ or}$$

$$\cos \phi = 1 - (C_1^2 + C_2^2 - 2 \cdot C_1 \cdot C_2 \cdot \cos \sigma)/2z^2 \tag{4}$$

Rearranging the terms yields:

$$\cos \phi = 1 - ((C_1 + C_2)^2 + 2 \cdot C_1 \cdot C_2 - 2 \cdot C_1 C_2 \cdot \cos \sigma)/2z^2$$

The equation can be rewritten as:

$$\cos \phi = [1-(\Delta C^2/2z^2)]-[2 \cdot C_1 \cdot C_2 \cdot (1-\cos \sigma)/2z^2] \quad (5)$$

Figure 12:
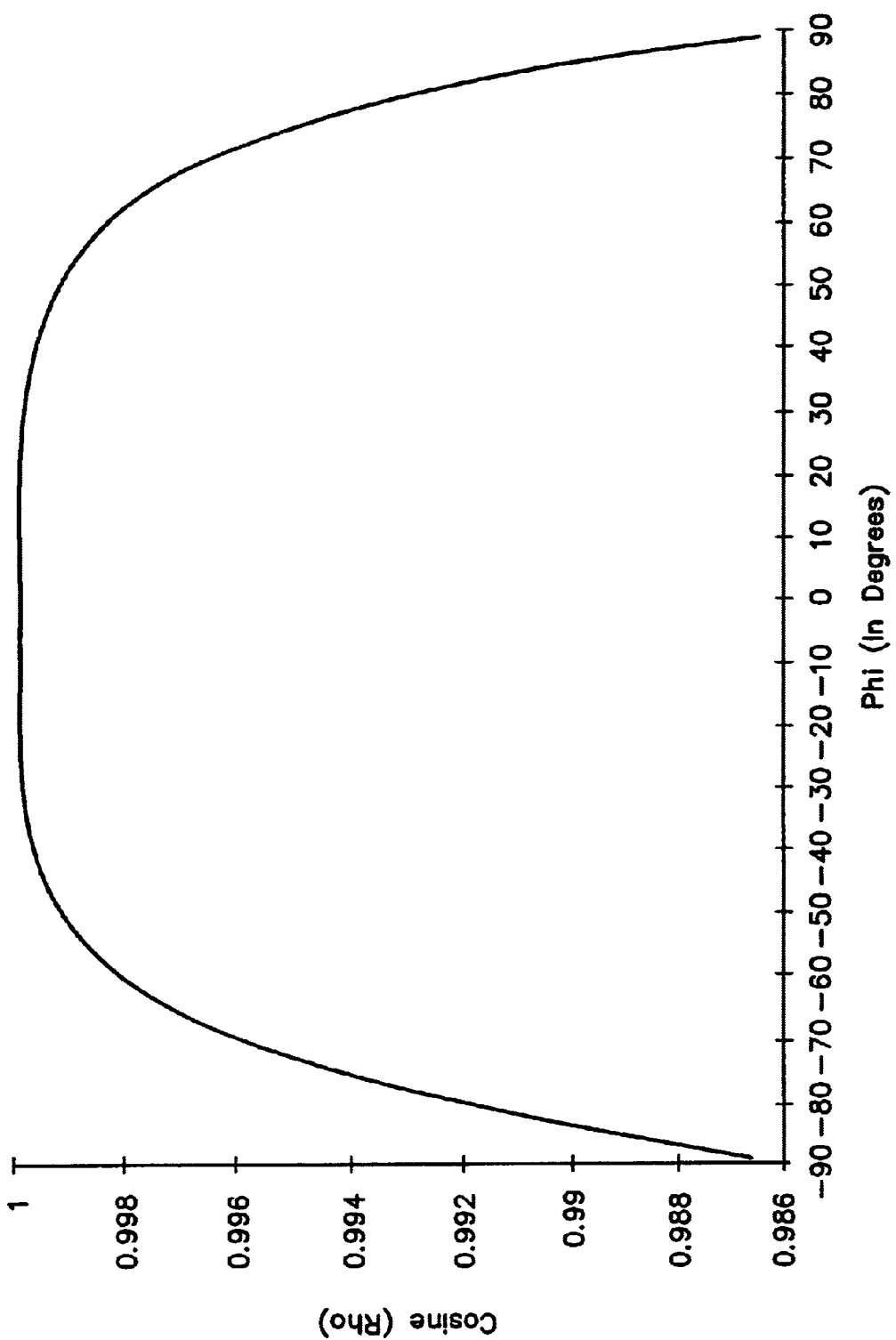
FIG. 12 is a graph of the magnitude of the cosine of the angle $\sigma$, as a function of the wrist angle $\Phi$ of FIGS. 10 and 111.

The difference in length between $C_1$ and $C_2$ is $\Delta C$. For cable lengths $C_1$ and $C_2$ typical for the proposed goniometer 100, a change in $\phi$ of $\pm 50°$ results in a change in $\sigma$ of $\sim \pm 3°$. FIG. 12 is a graph of the $\cos \sigma$ as a function of $\phi$, for the goniometer 100 as described and shown. For values of $\sigma$ of this magnitude, $\cos \sigma \rightarrow 1$, and the second term of the equation $\rightarrow 0$. The equation can thus be simplified to:

$$\phi = \cos_{-1}(1-\Delta C^2/2z^2). \quad (6)$$

Based on this mathematic simplification, angular displacement of the hand 102 relative to the forearm 104 in the R/U plane can be determined from differences in the cable lengths of the first and second cables 258 and 262 of the first and second displacement measuring devices 112 and 114. It will be understood that the trigonometric solution for angular displacement in the F/E plane can be calculated independently, in similar fashion, utilizing the relative differences in length of the second cable 262 and the third cable 268, as seen in FIG. 11. The length $C_3$ of the third cable 268 is simply substituted for $C_1$ in the above described equations.

The goniometer 100 may be easily applied to people with wrist anthropometry representative of the general population. Application of the goniometer 100 is simplified by the fact that determination of angular displacement is not dependent on location and alignment with the joint center of rotation X. This also may effectively improve accuracy considering that the wrist center of rotation X is dynamic, changing with wrist position, particularly in the F/E plane. The goniometer 100 could potentially be used to track the instantaneous center of rotation of the wrist X in either plane by rearranging the trigonometric solution.

Following application of the goniometer 100 to a person, angular displacement calculations can be used directly. However, as with any approach to joint goniometry, a brief data collection at a neutral position is recommended to allow correction for individual differences in fit and alignment. Referencing a neutral position also permits more appropriate comparison between people and on repeated measures within the same person.

Further improvement in system accuracy is possible through refinement of the hardware and/or enhancement of the trigonometric solution. The main assumption made in the algorithm development is that the angle $\sigma$ is small, and therefore $\cos \sigma - 1$ approaches zero, allowing simplification of equation (5) to equation (6). The addition of an "error term" accounting for the angle $\sigma$ could be introduced, but minimal improvement in accuracy would be expected, even at the extremes of range, based on the relationship presented in FIG. 12. Hardware refinement focusing on further improvement of fixation of the hand and forearm components 106 and 110, as well as efforts to improve comfort, optimization of system weight, durability, and displacement measuring device cable tension, should help to further improve usability and accuracy of the system. Accuracy could also be improved by increasing the distance between the hand and forearm components 106 and 110, effectively reducing the angle $\sigma$. Sensitivity could also be increased by increasing the distance between the cable ends z in either or both planes. However, increases in cable length or the distance between the cable ends require the tradeoff of increasing the size and inertia of the device.

From the foregoing description those skilled in the art will appreciate that numerous modifications may be made of this invention without departing from its spirit. For example, the cross-member and pylons of the hand component may be made as a single-piece unit. Moreover, the pylons could be replaced with one solid wall for attaching the free ends of the cables. The wall could have any suitable height or thickness and be made separate from the cross-member or as part of the cross-member. Therefore, the breath of the invention is not to be limited to the specific embodiments illustrated and/or described. Numerous modifications will occur to those skilled in the art, and therefore, the scope of the invention is to be determined by the appended claims and their equivalents.

What is claimed is:

1. A goniometer comprising:
   a forearm component having at least three displacement measuring devices, and adapted to be releasably attached to a forearm of a user;
   a hand component adapted to be releasably affixed to a hand of the user; and
   at least three cables extending from the displacement measuring devices and adapted to be releasably connected to the hand component,
   wherein the displacement measuring devices are configured to measure angular displacement of the hand component relative to the forearm component.

2. The goniometer of claim 1, wherein the displacement measuring devices are configured to measure the angular displacement of the hand component relative to the forearm component on both a radial/ulnar plane and a flexion/extension plane.

3. The goniometer of claim 2, wherein the cables are under constant tension when the goniometer is in use.

4. The goniometer of claim 2, wherein when the goniometer is in use on the hand and forearm of the user and viewed from above at least two of the cables are substantially parallel to each other.

5. The goniometer of claim 2, wherein when the goniometer is in use and on the hand and forearm of the user and viewed from a side of the hand at least two of the cables are substantially parallel to each other.

6. The goniometer of claim 2, wherein when the goniometer is in use on the hand and forearm of the user and viewed from a side of the hand at least two of the cables are substantially parallel to a volar aspect of the hand and the forearm of the user when the hand and forearm are in a natural flexion position.

7. The goniometer of claim 2, wherein at least the first and second cables extending from the forearm component are located at substantially a same height from a base of the forearm component.

8. The goniometer of claim 7, wherein the third cable extending from the third displacement measuring device is located at a height between the base of the forearm component and the first and second cables.

9. The goniometer of claim 1, wherein at least one of the displacement measuring devices is a potentiometer including a reel and one of the cables extending from the reel.

10. The goniometer of claim 9, wherein at least two of the displacement measuring devices are a first and a second potentiometer and at least the first and second cables extend from the first and second potentiometers provided at substantially a same height from a base of the forearm component.

11. The goniometer of claim 10, wherein the third displacement measuring device is a third potentiometer, and the third cable extends from the third potentiometer provided at a height between the base of the forearm component and the first and second cables.

12. The goniometer of claim 1, wherein the hand component is a unitary piece.

13. The goniometer of claim 12, wherein the cables are releasably attached to the hand component allowing for unrestrained rotation.

14. The goniometer of claim 1, wherein the hand component further comprises at least two pylons extending from the hand component for locating free ends of the cables.

15. The goniometer of claim 14, further comprising swivel joints releasably connecting each cable adjacent a top of a pylon.

16. The goniometer of claim 15, further comprising a swivel joint releasably connecting a third cable to a base of a pylon.

17. The goniometer of claim 14, wherein the hand component further comprises a cross member for locating the pylons on the hand component.

18. The goniometer of claim 17, wherein the hand component further comprises a bar for removably locating the cross member.

19. The goniometer of claim 18, wherein the bar further comprises slots provided along its length, and the cross member includes channels such that the cross member slidably engages the bar.

20. The goniometer of claim 19, wherein the cross member is adjustably secured to the bar with at least one screw.

21. The goniometer of claim 1, wherein the hand component further comprises a glove for removably attaching the hand component to the hand of the user.

22. The goniometer of claim 21, wherein the glove is a palmless glove.

23. The goniometer of claim 21, wherein the glove is a fingerless glove.

24. The goniometer of claim 21, wherein the hand component further comprises a bar secured to the glove.

25. The goniometer of claim 24, wherein the bar is secured to the glove such that the bar is adapted for location adjacent a volar surface of a third metacarpal of the hand of the user when the glove is placed on the hand of the user.

26. The goniometer of claim 1, wherein the forearm component further comprises a housing for mounting the displacement measuring devices.

27. The goniometer of claim 26, wherein the forearm component further comprises a cuff provided adjacent the housing and adapted for removable securement to the forearm of the user.

28. The goniometer of claim 27, wherein the cuff further comprises at least one hinge adapted for adjustment to the forearm.

29. The goniometer of claim 27, wherein the cuff is adapted to adjust to a cross-sectional area enclosed by the cuff.

30. The goniometer of claim 28, wherein the cuff is lined with orthotic foam.

31. The goniometer of claim 27, wherein the cuff further comprises a strap adapted to releasably secure the cuff to the forearm.

32. The goniometer of claim 27, wherein the cuff is a band.

33. The goniometer of claim 32, wherein the band is a loop.

34. The goniometer of claim 33, wherein the band is formed into a loop using hook-and-loop fastener.

35. A goniometer comprising:
a forearm component having at least three potentiometers adapted to be releasably affixed to a forearm of a user; and
a hand component adapted to be releasably affixed on a back of a hand of the user, the potentiometers adapted to be connected to the hand component,
wherein the potentiometers are configured to measure angular displacement of the hand component relative to the forearm component without calibration.

36. A method of determining wrist position in both flexion/extension and radial/ulnar deviation planes of movement, the method comprising the steps of:
providing a forearm component for locating three displacement measuring devices on a forearm of a user;
providing a hand component on the back of a hand of the user; and
connecting at least three cables, one from each displacement measuring device to the hand component;
wherein the displacement measuring devices are configured to measure angular displacement of the hand component relative to the forearm component in both the radial/ulnar and flexion/extension planes.

37. The method of claim 36, further comprising the step of:
connecting the first, second and third cables to the hand component such that they are under constant tension.

38. The method of claim 36, the step of connecting further comprising:
locating at least the first and second cables at substantially the same height from a base of the forearm component.

39. The method of claim 38, the step of connecting further comprising:
locating the third cable at a height between the base of the forearm component and the first and second cables.

40. The method of claim 36 wherein one of the displacement measuring devices includes a first potentiometer including a reel and one of the first, second and third cables extending from the reel.

41. The method of claim 40, the step of connecting further comprising:
providing a second potentiometer with the second displacement measuring device; and
connecting the first and second cables from the first and second potentiometers to the hand component such that the cables are located at substantially the same height from a base of the forearm component and are substantially parallel to each other.

42. The method of claim 41, the step of connecting further comprising:
providing a third potentiometer with the third displacement measuring device; and
extending the third cable from the third potentiometer to locate the third cable at a height between the base of the forearm component and the first and second cables such that the third cable is substantially parallel to at least one of the first and second cables.

43. The method of claim 36, the step of providing a hand component further comprising:
providing at least two pylons for connecting ends of the cables to the hand component.

44. The method of claim 43, the step of connecting further comprising:
connecting the cables to the pylons with swivel joints.

45. The method of claim 43, the step of connecting further comprising:
attaching the cables to the pylons to allow for unrestrained rotation.

46. The method of claim 43, the step of connecting further comprising:

provide a cross-member for locating the pylons on the hand component.

47. The method of claim 46, the step of connecting further comprising:

removably locating the cross-member o n a bar of the hand component.

48. The method of claim 36, the step of providing the hand component further comprising:

attaching the hand component onto a glove for removably locating the hand component on the back of the hand of the user.

49. The method of claim 36, the step of providing the hand component further comprising:

locating the hand component such that it is adjacent a volar surface of the third metacarpal on the hand of the user.

50. The method of claim 36, the step of providing the forearm component further comprising:

mounting the displacement measuring devices on a housing of the forearm component.

51. The method of claim 36, the step of providing the forearm component further comprising:

securing the forearm component to the forearm of the user by a cuff.

52. The method of claim 51, the step of providing the forearm component further comprising:

adjusting cross-sectional area enclosed by the cuff.

53. The method of claim 51, the step of providing the forearm component further comprising:

releasably securing the cuff to the forearm of the user with a hook-and-loop fastener.

54. The method of claim 36, further comprising the step of:

measuring the linear displacement of the first, second and third cables as the hand moves from a first position to a second position.

55. The method of claim 54, further comprising the step of:

calculating the angular displacement of the hand component relative to the forearm component in both the radial/ulnar and flexion/extension planes by using the measured linear displacement of the cables relative to one another.

* * * * *